(12) United States Patent
Pridgeon et al.

(10) Patent No.: US 8,080,648 B1
(45) Date of Patent: Dec. 20, 2011

(54) PESTICIDAL DOUBLE STRANDED RNA COMPOSITION AND METHOD OF USE THEREOF

(75) Inventors: Julia W. Pridgeon, Newberry, FL (US); James J. Becnel, Gainesville, FL (US); Daniel A. Strickman, Hyattsville, MD (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 1123 days.

(21) Appl. No.: 11/716,499

(22) Filed: Mar. 9, 2007

(51) Int. Cl.
*C07H 21/02* (2006.01)
*C07H 21/04* (2006.01)
*C12Q 1/68* (2006.01)
*C12P 19/34* (2006.01)
*C12N 5/00* (2006.01)

(52) U.S. Cl. .......... 536/24.5; 435/6; 435/91.1; 435/325; 435/375

(58) Field of Classification Search ............. 435/6, 91.1, 435/325, 375; 536/24.5
See application file for complete search history.

(56) References Cited

U.S. PATENT DOCUMENTS 6,506,559 B1    1/2003   Fire et al.

OTHER PUBLICATIONS

Attardo et al. (PNAS, 2003 vol. 100, No. 23:13374-13379).*
Martin et al. Molecular and Cellular Biology, 2001 vol. 21, No:1:164-174).*
Jones et al. (Journal of Biological Chemistry, 2000 vol. 275, No. 29:22157-22165).*
Hammond et al. (Nature Reviews Genetics 2001, vol. 2:110-119).*
Wheeler et al. (Nature Methods, 2004 vol. 1, No:2:1-6).*
Hay et al. (Cell, 1995 vol. 83:1253-1262).*
GenBank Accession No. DQ993355, submitted Sep. 13, 2006, downloaded from http://www.ncbi.nlm.nih.gov/nuccore/dq993355 on Mar. 22, 2011.*
Elbashir et al. (Methods, 2002 vol. 26:199-213).*
Pridgeon et al. (J. Med. Entomol., 2008, 45(3) 414-420).*
Pridgeon et al. (Journal of Med. Entomol. 45(3) 414-420, 2008).*

* cited by examiner

*Primary Examiner* — Terra Cotta Gibbs
(74) *Attorney, Agent, or Firm* — John Fado; Albert Y. Ysui; Lesley Shaw

(57) ABSTRACT

A pesticidal compound that regulates programmed cell death pathways via the topical application of double strand RNA is disclosed. The compound is constructed as a specific-target pesticide that is a biosafe nucleic acid pesticide for pest control.

6 Claims, 8 Drawing Sheets

PESTICIDAL DOUBLE STRANDED RNA COMPOSITION AND METHOD OF USE THEREOF

FIELD OF THE INVENTION

This invention relates to a pesticide that regulates programmed cell death pathways via RNA interference through the application of double stranded RNA to a targeted pest.

BACKGROUND OF INVENTION

Insects and other pests cost farmers billions of dollars annually in crop losses and the expense of keeping these pests under control. The damage caused by insect pests result in decrease crop yield and reduction of crop quality, ultimately leading to an overall increase in agricultural farming costs. To combat insect pest, chemical pesticides are utilized to prevent or mitigate against crop destruction. However, use of chemical pesticides has its disadvantages. Disadvantages include indiscriminate insect eradication which results in extermination of non-target, beneficial insect species. Chemical pesticide usage also leads to chemical residue run-off into streams and seepage into water supplies resulting in environment damage. Crop or insects consumed having chemical residues present a danger to animals higher up on the food chain. The handling and application of chemical pesticides also presents a danger as there is a possibility of accidental exposure to people handling the chemical pesticides or accidental disbursal into an unintended environmental area. In addition, prolonged chemical pesticide application results in the targeted-surviving pest developing an evolutionary resistance to the chemical pesticide. In order to eradicate the resistant-pest, a cycle of even more potent chemical pesticides are utilized, resulting in more environmental damage and eventually an even more chemical-resistant pest. As such there is a need in the art to control pest populations without the disadvantages of chemical pesticides.

An approach to decrease agricultural dependence of chemical pesticides is gene targeting of functional nucleic acids of target-pests by either over expressing or silencing gene expression. One approach is to utilize RNA interference pathways to knockdown essentially any gene of interest via double strand RNA. Double strand RNA (dsRNA) induces sequence—specific posttranscriptional gene silencing in many organisms by a process known as RNA interference (RNAi). RNAi is a post-transcriptional, highly conserved process in eukaryotes that lead to specific gene silencing through degradation of the target mRNA. The silencing mechanism is mediated by dsRNA that is homologous in sequence to the gene of interest. The dsRNA is processed into small interfering RNA (siRNA) by an endogenous enzyme call DICER inside the target pest, and the siRNAs are then incorporated into a multi-component RNA-induced silencing complex (RISC), which finds and cleaves the target mRNA. The dsRNA inhibits expression of at least one gene within the target, wherein inhibition of the gene exerts a deleterious effect upon the target.

Fire, et al. (U.S. Pat. No. 6,506,559) discloses a process of introducing RNA into a living cell to inhibit gene expression of a target gene in that cell. The RNA has a region with double-stranded structure. Inhibition is sequence-specific in that the nucleotide sequences of the duplex region of the RNA and of a portion of the target gene are identical. Specifically, Fire discloses a method to inhibit expression of a target gene in a cell in vitro comprising introduction of a ribonucleic acid into the cell in an amount sufficient to inhibit expression of the target gene, wherein the RNA is a double-stranded molecule with a first strand consisting essentially of a ribonucleotide sequence which corresponds to a nucleotide sequence of the target gene and a second strand consisting essentially of a ribonucleotide sequence which is complementary to the nucleotide sequence of the target gene, wherein the first and the second ribonucleotide strands are separate complementary strands that hybridize to each other to form said double-stranded molecule, and the double-stranded molecule inhibits expression of the target gene.

Since dsRNA has different effectiveness in gene knockdown, utilizing RNA interference technique to develop an effective pesticide poses a challenge. In some instances, robust knockdown occurs, while other instances results in no knockdown despite efficient transfection. In addition, when a target protein is very abundant in an organism or has a very long half-life (days to weeks), the obvious RNAi effect will be difficult to observe. Liu, et al. (U.S. Pat. No. 6,846,482) discloses an expression vector engineered to produce dsRNA within a pest. Salient to Liu is contacting an insect with a recombinant baculovirus wherein a first ribonucleic acid whose sequence corresponds to at least a portion of at least one gene endogenous to the insect to control the insect. Given the advances made in the field of transfection efficiency and RNA interference, there is a need in the art to utilize the advances without a baculovirus as a vector. Such a method would mediate control of a target-pest without depending on variables associated with a baculovirus, such as utilizing baculoviruses that are host specific.

To utilize RNA interference as a method to regulate a gene expression, a specific biological pathway needs to be targeted. One such explored pathway is apoptosis. Apoptosis is an evolutionarily conserved pathway of cell suicide that is critical for development and homeostasis of an organism. Apoptosis is the deliberate programmed cell death in multicellular organisms. Suicidal cell death is orderly biochemical programmed cell death where cellular signals determine whether there is a deliberate life relinquishment by the cell. The balance between positive signals (surviving signals) and negative signals (death signals) decides whether a cell should commit suicide. Regulation of programmed cell death pathways facilitates a method to utilize a nucleic acid pesticide for pest control by either developing nucleic acid pesticides for promoting the expression of pro-apoptotic factors (gene overexpression) and/or develop nucleic acid pesticide to reduce the expression of anti-apoptotic factors (gene silencing) so that the pest will die. By utilizing the targeted-pest cell death pathway, there will be less dependence on chemically based pesticides for pest control.

Apoptosis was first experimentally examined in the breakdown of the intersegmental muscles of silkworm, *Bombyx mori* (L.) Cells undergoing apoptosis have distinguishing characteristics, such as cell shrinkage, genomic DNA fragmentation, chromatin degradation and condensation, circular cellular character indication of caspases activation, pyknosis, or karyorrhexis. Researchers have identified molecular components of the cell death machinery that involve cysteine aspartic acid proteases, for example caspase-9, caspase-3, caspase-7, caspase-8, and/or caspase-10. Other molecular components include Fas receptors, Bcl-2 and Bax proteins. In addition, there are other proteins, such as inhibitor of apoptosis (IAP) and second mitochondria-derived activator of caspases (SMAC) that regulate the apoptotic process.

Programmed cell death can be triggered by internal signals through the intrinsic mitochondrial pathway. In a healthy cell, the outer membrane of the mitochondria displays the apoptosis suppressing protein Bcl-2 on its surface. Internal cellular perturbation causes Bcl-2 to activate a related protein, Bax to puncture the outer mitochondrial membrane causing the heme protein, cytochrome c, to be released by the mitochondria. The release of cytochrome c binds to the cytosolic protein apoptotic protease activating factor-1 (Apaf-1). Using energy provided by ATP, these complexes aggregate to form apoptosomes. Apoptosomes then bind to and activate the cysteine protease caspase-9. Caspase-9 is one of a family of over a dozen caspases. Caspase-9 cleaves and activates caspase-3 and caspase-7. The activation of these executioner caspases creates an expanding cascade of proteolytic activity which leads to digestion of structural proteins in the cytoplasm and degradation of chromosomal DNA, and phagocytosis of the cell. The art discloses various proteins involved in the apopotosis pathway. For instance, Nunez et al. (U.S. Pat. No. 6,348,573) discloses a protein sequence for RIP-like interacting CLARP kinase that functions as a positive regulator of apoptosis.

Programmed cell death can also be triggered by external signals through the extrinsic or death receptor pathway. Signal molecules such as Apo-1 or CD95, (Fas) and Tumor necrosis factor (TNF) receptor are integral membrane proteins with receptor domains exposed at the surface of the cell. Binding of their respective complementary death activators FasL and TNF transmits a signal to the cytoplasm that leads to activation of caspase 8. Caspase 8 initiates a cascade of effector caspase activation and the positive feedback of biological perturbation eventually leads to phagocytosis of the cell.

Programmed cell death can also be triggered by apoptosis-Inducing Factor (AIF). AIF is a flavoprotein that is a mitochondria factor released during apoptosis that is normally located in the intermembrane space of mitochondria. Unlike intrinsic or extrinsic mitochondria pathways, cysteine-aspartic-acid-proteases are not utilized to initiate apoptosis with AIF. When the cell receives a sign for apoptosis, AIF is released from the mitochondria and translocates into the nucleus to bind to DNA. Experiments have shown that caspases are not involved in AIF-activated apoptosis pathway. DNA binding by AIF stimulates chromatin condensation and DNA fragmentation. DNA binding by AIF occurs through a distinct domain of the protein in a manner that does not rely on specific DNA sequences. AIF also has another domain that acts as an NADH oxidase, a redox enzyme. The NADH oxidase activity of AIF is separable from its DNA-binding activity and is not required for AIF to induce apoptosis. Given the knowledge of apoptosis pathways, there is a need to utilize the knowledge to target specific pathways for pest control.

Another family of apoptosis regulatory proteins are inhibitor of apoptosis proteins (IAPs). IAP suppresses apoptosis by preventing the activation of procaspases and endogenously inhibits the enzymatic activity of mature caspases. IAPs were originally discovered in insect baculoviruses (Cydia pomonella granulosis virus and Orgyia pseudotsugata nuclear polyhedrosis virus) (Birnbaum, M J. et al., 1994. *Journal of Virology*, 68:2521-2528; Clem R J. et al., 1994. *Mol. Cell Biol*, 14:5212-5222; Crook N E. et al., 1993. *Journal of Virology*, 67:2168-2174). Since their first reports in baculoviruses, IAPs have been identified in many other organisms, such as mosquito iridescent viruses (Delhon G. et al., 2006. *Journal of Virology*, 80:8439:8449), insects (Hay B A. et al., 1995. *Cell*, 83:1253-1262; Muro I. et al., 2002. *J. Biol Chem*, 277:49644-49650), yeast (Walter D. et al., 2006. *J. Cell Sci.*, 1843:1851), and humans (Ambrosini G. et al., 1997. *Nat. Med.*, 3:917:921; Liston P. et al., 1996. *Nature*, 379:349:353; Vitte-Mony I. et al., 1997. *J. Biol. Chem.*, 273: 33915-33921). Many IAPs are capable of blocking apoptosis when overexpressed in cells in a plurality of species (Beidler D R. et al., 1995. *J. Biol. Chem.*, 270:16526-16528, Hawkins C J., et al., 1996. *Cell Death Differ.*, 5:569-576). The exact molecular mechanisms by which IAPs inhibit apoptosis are still under investigation, however, it has been shown that IAPs are able to inhibit the activity of cysteine proteases that cleaves different target proteins. IAPs are capable of blocking apoptosis through direct inhibition of proapoptotic proteins, such as Reaper, HID, and GRIM in *Drosophila* (Vucic D. et al., 1998. *J. Biol. Chem.*, 273:33915-33921; Vucic D. et al., 1998. *Mol. Cell Biol.*, 3300-3309b, Vucic D. et al., 1997. *Proc. Natl. Acad. Sci. USA*, 94:10183-10188).

In *Drosophila*, four IAPs (DIAP1, DIAP2, deterin, and bruce) have been reported (Hay B A. et al., 1995. *Cell*, 83:1253:1262; Jones G. et al., 2000. *J. Biol. Chem.*, 275: 22157-22165; Vernooy S Y. et al., 2002. *Curr. Biol.*, 12:1164-1168). Four other insect IAP1s have also been identified, namely TnIAP1 from the cabbage looper *Trichoplusia ni* (Seshagiri S. et al., 1999. *J. Biol. Chem.*, 274:36769-36773), SfIAP1 from the fall armyworm *Spodoptera frugiperda* (Huang Q. et al., 2000. *Proc. Natl. Acad. Sci. USA*, 97:1427: 1432), BmIAP from the silkworm *Bombyx mori* (Huang Q. et al., 2001. *Biochim. Biophys. Acta.*, 1499:191-198), and AtIAP1 from the mosquito *Aedes triseriatus* (Blitvich B J. et al., 2002. *Insect Mol. Biol.* 11:431:442).

Baculovirus IAP genes include sequences encoding a ring zinc finger-like motif, which is presumed to be directly involved in DNA binding, and two N-terminal domains that consist of a 70 amino acid repeat motif termed a BIR domain (Baculovirus IAP Repeat). The inhibitor of apoptosis proteins typically have one to three baculovirus IAP repeat (BIR) domains. The BIR domain is essential for anti-apoptotic activity (Takahashi R. et al., 1998. *J. Biol. Chem.*, 273:7787: 7790; Walter D. et al., 2006. *J. Cell Sci.*, 119:1843-1851). Approximately 70 amino acids in length containing a conserved stretch of cysteines and histidines, BIR domain is well-known for its ability to bind and inhibit caspases (Takahashi et al., supra) and mediate protein-protein interaction (Hozak R R. et al., 2000. *Mol. Cell. Biol.*, 20:1877-1885). As such, efforts to utilize mammalian IAPs have been disclosed. For example, Korneluk et al. (U.S. Pat. No. 6,156,535) discloses a substantially pure DNA encoding mammalian IAP polypeptides and methods of using such DNA to express the IAP polypeptides in cells and animals to inhibit apoptosis. Additionally, Rothe et al. (U.S. Pat. No. 6,821,736) discloses human cellular IAPs having a series of defined structural domain repeats and/or a RING finger domain.

Furthermore, Shi et al. (U.S. Pat. No. 6,992,063) discloses peptides and peptidomimetics capable of modulating apoptosis through their interaction with cellular IAPs (inhibitor of apoptosis proteins). The peptides and mimetics are based on the N-terminal tetrapeptide of IAP-binding proteins, such as Smac/DIABLO, Hid, Grim and Reaper, which interact with a specific surface groove of IAP. Shi discloses a compound that binds a BIR-3 domain of IAP and relieves IAP mediated inhibition of caspase activity.

Regulating programmed cell death pathways to develop nucleic acid pesticides has an advantage over conventional chemical-based pesticides inasmuch as nucleic acid pesticides developed through regulating the programmed cell death pathways are specific in terms of pest target. Unlike traditional chemical pesticides, a nucleic acid pesticide is designed to produce specific gene product for one species, thus not affecting non-target organisms. In addition, the utilization of nucleic acid pesticide will maximize safety and minimize environmental impact. As such, there is a need in the art for a method utilizing a nucleic acid pesticide that operates via the apoptosis pathway.

Furthermore, a novel control method will be very effective against resistant species since the engineered nucleic acid pesticides would be specific against resistant pest species. A need exists in the art for a method of producing a pesticide utilizing nucleic acid as a pesticide. In addition, there is a need for a method for producing a pesticide by regulating programmed cell death pathways to develop nucleic acid pesticides for pest control.

BRIEF SUMMARY OF THE INVENTION

The novelty of this invention is the construction of nucleic acid products that target specific insect pests. An embodiment of the invention is nucleic acid products that bind with the endogenous mRNA that encode IAP of a targeted insect.

In one aspect of the invention, the method for producing a pesticidal nucleic acid product comprises selecting a biological sample for pest control, cloning a gene of interest from the biological sample, constructing a nucleic acid product wherein said product is sufficiently complementary to said gene and induces ribonucleic acid interference, resulting in target pest mortality. In one embodiment, the nucleic acid product is double stranded ribonucleic acid. In another embodiment, the nucleic acid product is small interfering ribonucleic acid. In yet another embodiment, the gene of interest encodes an inhibitor of apoptosis protein. In another embodiment, the nucleic acid product hybridizes with target pest messenger ribonucleic acid, said messenger ribonucleic acid transcribes a polypeptide having at least one baculoviral inhibitor of apoptosis repeat domain. In yet another embodiment, the nucleic acid product hybridizes with target pest messenger ribonucleic acid, said messenger ribonucleic acid transcribes a polypeptide having at least one ring zinc finger domain. In another embodiment, the target pest is of the order of diptera. In another embodiment, the target pest is *Aedes aegypti*. In yet another embodiment, the biological sample and target pest are the same species. In yet another embodiment, the invention is a composition comprising the double stranded ribonucleic acid and a carrier. In one embodiment, the double stranded ribonucleic acid is at a concentration of about 0.01% to 0.04% of the composition.

In another aspect of the invention, the application of a nucleic acid product having pesticide activity, comprises selecting a biological sample for pesticide control, cloning a gene of interest from the biological sample, constructing a nucleic acid product wherein said product is sufficiently complementary to said gene; and contacting an effective amount of said nucleic acid product to a target-pest wherein the target-pest population is controlled. In one embodiment, the nucleic acid product is double stranded ribonucleic acid. In another embodiment, the nucleic acid product is small interfering ribonucleic acid. In yet another embodiment, the gene of interest encodes an inhibitor of apoptosis protein. In another embodiment, the nucleic acid product hybridizes with target pest messenger ribonucleic acid, said messenger ribonucleic acid transcribes a polypeptide having at least one baculoviral inhibitor of apoptosis repeat domain. In yet another embodiment, the nucleic acid product hybridizes with target pest messenger ribonucleic acid, said messenger ribonucleic acid transcribes a polypeptide having at least one ring zinc finger domain. In another embodiment, the target pest is of the order of diptera. In another embodiment the target pest is *Aedes aegypti*. In another embodiment the biological sample and target pest are the same species. In yet another embodiment, the invention is a composition comprising the double stranded ribonucleic acid and a carrier. In an embodiment, the double stranded ribonucleic acid is at a concentration of about 0.01% to 0.04% of the composition.

BRIEF DESCRIPTION OF THE DRAWING

The present invention together with the disclosed embodiments and may best be understood from the following detailed description of the drawings, wherein.

DETAILED DESCRIPTION OF THE INVENTION

Submission on Compact Disc

Figure 1:
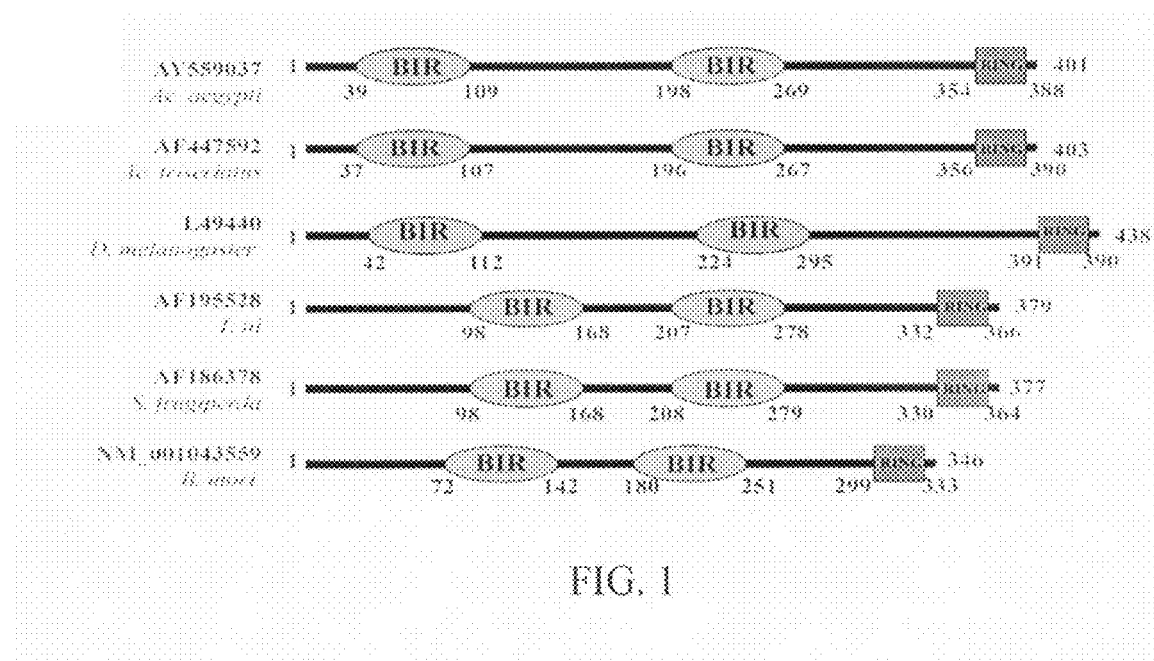
FIG. 1 is a comparison of conserved domains of insect IAP1s. Conserved domains were predicted by the SMART program and the diagram was drawn to scale for amino acid length. The amino acid span of each conserved domain was marked below each domain. All numbers represent amino acid position.

The contents of the following submission on compact discs are incorporated herein by reference in its entirety: a copy of the Sequence Listing and two copies computer readable form copy of the Sequence Listing on compact disc, each containing: file name: "Table 1 ST25.txt" as a sequence listing, date recorded: Mar. 6, 2007, size: 2.27 KB.

Disclosed here is the novel method of developing nucleic acid pesticides by regulating programmed cell death pathways. Using double strand RNA inhibiting IAP gene as a nucleic acid pesticides, a novel method to develop nucleic acid pesticides for pest control is disclosed.

Definitions

As used in the specification and claims, the singular form "a", "an" and "the" include plural references unless the context clearly dictates otherwise. For example, the term "a cell" includes a plurality of cells, including mixtures thereof.

The term "apoptosis" means orderly programmed cell death that takes place in metazoan cells following activation of an intrinsic cell suicide program that results in cellular transmission of dying cells to phagocytes. Apoptosis is a process in the development and homeostasis of metazoan animals. Apoptosis involves characteristic changes, that including cell shrinkage, blebbing of the plasma membrane, and DNA fragmentation. Detachment of cell line from the cell culture substrata is also an indication of apoptosis.

The term "inhibitor of apoptosis protein" or "IAP" refers to is a term to mean a protein that prevents the onset of cellular apoptosis. The protein is characterized by having at least one baculovirus IAP repeat motifs, comprising an approximately 70 amino acid residue zinc-binding domain. IAPs have functional activity by binding to caspases, such as caspase 3, 7, and 9.

The term "gene" refers to a DNA sequence involved in producing a polypeptide or precursor thereof. The polypeptide can be encoded by a full length coding sequence or by any portion of the coding sequence, such as exon sequences, such that the targeted enzymatic activity is retained.

The term "oligonucleotide" refers to a molecule comprising a plurality of deoxyribonucleotides or ribonucleotides. Oligonucleotide may be generated in any manner, including chemical synthesis, DNA replication, reverse transcription, polymerase chain reaction, or a combination thereof. The present invention embodies utilizing the oligonucleotide in the form of double-stranded RNA as pesticide for pest control. Inasmuch as mononucleotides are synthesized to construct oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficient complementary with the sequence of the template to hybridize and thereby form a template primer complex for synthesis of the extension product of the primer.

The term "double stranded RNA" or "dsRNA" refers to two substantially complementary strands of ribonucleic acid. "Small interfering RNA" or "siRNA" refers to a short double-strand of ribonucleic acid, approximately 20 to 30 nucleotides in length. The term "RNA interference" or "RNAi" refers to a cellular mechanism for the destruction of targeted ribonucleic acid molecules. Under endogenous conditions, RNAi mechanism operates when dsRNA is cleaved to siRNA via an enzyme, DICER. The siRNA is processed to a single stand of anti-sense ribonucleic acid and coupled with a protein complex named RISC. The antisense RNA then targets a complementary gene constructs, such as messenger RNA that is cleaved by ribonuclease.

As used herein, "knock-down" is defined as the act of binding an oligonucleotide with a complementary nucleotide sequence of a gene as such that the expression of the gene or mRNA transcript decreases. In an embodiment, knock-down of an IAP gene occurs via a topical application of dsRNA.

The term "substantially single-stranded" when used in reference to a nucleic acid product means that the product molecule exists primarily as a single strand of nucleic acid in contrast to a double-stranded product which exists as two strands of nucleic acid which are held together by inter-strand base pairing interactions.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

The term "corresponds to" as used herein means a polynucleotide sequence homologous to all or a portion of a reference polynucleotide sequence, or a polypeptide sequence that is identical to a reference polypeptide sequence. In contradistinction, the term "complementary to" is used herein to mean that the complementary sequence is homologous to all or a portion of a reference polynucleotide sequence. For example, the nucleotide sequence "TATAC" corresponds to a reference sequence "TATAC" and is complementary to a reference sequence "GTATA".

"Supernatant" refers to the liquid broth remaining when cells grown in broth are removed by centrifugation, filtration, sedimentation, or other means well known in the art.

An "effective amount" is an amount sufficient to effect beneficial or desired results. An effective amount can be administered in one or more administrations. In terms of treatment, an "effective amount" is that amount sufficient to control the behavior of a target pest by causing an adverse effect on that pest, including (but not limited to) physiological damage to the pest; inhibition or modulation of pest growth; inhibition or modulation of pest reproduction; or death of the pest. A product is "pesticidal" if it kills at least one individual in a pest population. In an embodiment where siQuest+dsRNA IAP-D nucleic acid product was topically applied to target pests, 52% of the target pests died over a 24 hour period. In another embodiment where siQuest+dsRNA IAP-D nucleic acid product was topically applied to target pests, 72% of the target pests died over a 48 hour period.

Additionally, a nucleic acid product may be non-lethal at a particular concentration or amount. An effective concentration may range from 1:1 to 16:1 volumetric ratio of carrier to nucleic acid product. An embodiment of acetone:dsRNA IAP-C having a volumetric ratio of 1:1 resulted in a 23% mortality rate. In another embodiment of acetone:dsRNA IAP-D having a volumetric ratio of 2:1 resulted in a 23% mortality rate. Additionally, an effective concentration may range from 1:1:1:1 to 16:1:1:1 volumetric ratio of carrier to three nucleic acid products. An embodiment of acetone:IAP-B:IAP-C:IAP-D having a volumetric ratio of 1:1:1:1 resulted in a 30% mortality rate. An embodiment of acetone:IAP-B:IAP-C:IAP-D having a volumetric ratio of 4:1:1:1 resulted in a 37% mortality rate.

The term "pesticide" refers to any substance that affects the mortality of a insect. A pesticide can comprise of chemical pesticides wherein active inorganic chemicals are toxic towards an insect pest. A pesticide can also comprise of a nucleic acid product that inhibits endogenous gene expression of a targeted insect pest, resulting in targeted insect fatality.

The term "solvent" includes any liquid that holds another substance in solution. Examples of solvents include organic solvents such as acetone and ethanol. The term "carrier" includes any substance that carries the nucleic acid product into the insect body. An example of a carrier includes siQuest transfection reagent and solvents of acetone and ethanol.

Detail Description of the Invention

The Orlando strain of *Aedes aegypti* was reared in the insectary of the Mosquito and Fly Research Unit at the Center for Medical, Agricultural, and Veterinary Entomology, USDA-ARS and the adults were used for total RNA extraction.

Total RNA Extraction

Total RNA was extracted from specimen using TRIzol Reagent (Invitrogen, Carlsbad, Calif.). Specifically, 20 ml of Trizol and 1.92 gm of adult mosquitoes were added into a 50 ml tube and homogenized with a power homogenizer. The homogenate was transferred to twenty 1.5 ml tubes and incubated at room temperature 5 minutes to permit the complete disassociation of nucleoprotein complexes. For phase separation, 0.2 ml of chloroform was added to each tube and vortexed and incubated at room temperature for two to three minutes. The homogenate was centrifuged at 4° C. for 15 minutes and 14,000 rpm, wherein the aqueous phase was transferred to 1.5 ml tubes. The resulting pellet contained extra-cellular membrane, polysaccharides, and high molecular weight DNA while the supernatant contains RNA. For RNA precipitation and wash, 0.5 ml of isopropyl alcohol were added to each tube, vortexed, and incubated at room temperature for 10 minutes. Thereafter, each tube was centrifuged at 4° C. for 10 minutes at 14,000 rpm. The RNA pellet was washed with 75% ethanol and air-dried. The RNA pellet was redissolved in 100 µl of DEPC treated water with the RNA combined into a 15 ml tube. Total RNA was stored at −80° C.

mRNA Isolation

Annealing of the oligo-dt probe to Total RNA was completed using PolyATract mRNA Isolation systems, specifically the Promega (III) Z5300. RNA was isolated using Oligotex-dT suspension (QIAGEN, Valencia, Calif.). In a sterile, ribonuclease-fee 1.5 ml tube, 500 µl of Total RNA was added and plated on a heating block (65° C.) for 10 minutes. 3 µl of Biotinylated-Oligo(dt) probe and 141 of 20×SSC was added to the tube and incubated at room temperature until completely cooled.

One tube of Streptavidin-Paramagnetic particles (SA-PMPs) (0.6 ml) was placed on a magnetic separation stand until the SA-PMPs assembled to one side of the test tube. The supernatant was removed and repeated three time with 0.5× SSC (300 µl per wash). The SA-PMPs was resuspended in 100 µl of 0.5×SSC.

Contents of annealed oligo(dT)-mRNA hybrids were added to a tube containing washed SA-PMPs and incubated at room temperature for 10 minutes to capture and wash Annealed Oligo(dT)-mRNA hybrids. The tube was mixed in the interim every 1-2 minutes. The SA-PMPs were captured via a magnetic separation and the supernatant was removed. The particles were then washed four times with 300 µl of 0.1×SSC.

The final SA-PMP pellet was resuspended in 100 µl $H_2O$ with the SA-PMPs magnetically captured and eluted mRNA was transferred to separate tube. The SA-PMP was resuspended in 150 µl of $H_2O$ with the SA-PMPs subjected to magnetic capture with resulting eluted mRNA pooled with captured mRNA. The mRNA was prepped for cDNA cloning by adding 70 µl of 3M sodium acetate (pH 5.2) with 800 µl of isopropanol to the mRNA, mixed and incubated at −20° C. overnight. The mRNA was then further concentrated via alcohol precipitation by centrifuging the mRNA at 14,000 rpm for 15 minutes with the pellet washed with 75% ethanol. The pellet was air-dried and resuspended in 30 µl of $H_2O$.

cDNA Synthesis cDNA synthesis was accomplished using GeneRacer Kit (Invitrogen). The mRNA was dephosphorylated using calf intestinal phosphatase (CIP). 250 ng of mRNA was added with DEPC $H_2O$, 10×CIP buffer, RNaseOUT (40 U/µl), and CIP (10 U/µl) for a total of 10 µl were mixed into a PCR tube and incubated at 50° C. for one hour.

The mRNA was precipitated via the addition of 90 µl of DEPC $H_2O$ and 100 µl phenol:chloroform to dephosphorylated RNA. The solution was vortexed and centrifuged at 14,000 rpm for 5 minutes at room temperature. The aqueous top phase (−1000 was transferred to a separate centrifuge tube. 2 µl of mussel glycogen (10 mg/ml) and 10 µl of 3M sodium acetate (pH 5.2) were mixed with the dephosphorylated RNA. 250 µl of 100% ethanol was vortex with the solution and stored overnight at −80° C. To pellet the mRNA, the solution was centrifuged at 14,000 rpm for 20 minutes with the resulting RNA pellet being washed with 75% ethanol and air-dried. The pellet was resuspended in 7 µl DEPC $H_2O$.

7 µl of dephosphorylated mRNA was added to a 0.5 ml PCR tube along with 1 µl of 10×TAP buffer, 1 µl of RNase Out (40 U/µl), and 1 µl of TAP (0.50 U/µl) for a total volume of 10 µl for removal of mRNA CAP structure. The solution was incubated at 37° C. for one hour. The RNA was precipitated via adding 90 µl of DEPC $H_2O$ and 100 µl of phenol:chloroform and in the same manner to the precipitation step subsequent to cDNA synthesis.

7 µl of decapped, dephosphorylated mRNA was added to GeneRacer RNA Oligo tube for ligation reaction of RNA Oligo to 5' end of mRNA. The solution was incubated at 65° C. for 5 minutes to relax the RNA secondary structure and then subsequently chilled for 2 minutes. The following were then added: 1 µl of ligase buffer, 1 µl of 10 mM ATP, 1 µl of RNase Out (40 U/µl), and 1 µl of T4 RNA Ligase (5 U/µl) for a total volume of 10 µl and was incubated for 1 hour at 37° C. The RNA was precipitated via conventional means by adding 90 µl DEPC H₂O, 100 µl phenol:chloroform (1:1), centrifuged with the top aqueous layer removed and transferred to a separate tube. 2 µl of mussel glycogen (10 mg/ml) along with 10 µl of 3M sodium acetate (pH 5.2), and 250 µl of 100% ethanol was added with the solution maintained at −80° C. for 30 minutes followed by centrifugation at 4° C. for 20 minutes. The resulting pellet was washed with 75% ethanol, air-dried, and resuspended in 10 µl of DEPC H₂O.

1 µl of GenRacer primer and 1 µl of dNTP Mix (10 mm) was added to ligated RNA in preparation for reverse Transcribing mRNA to cDNA. The solution was incubated at 65° C. to remove RNA secondary structure and chilled on ice for 2 minutes. 4 µl of 5× First Strand buffer, 2 µl of 0.1M DTT, 1 µl of RNaseOut (40 U/µl), 1 µl of SuperScript II RT (200 U/µl) was added to 1 µl of ligated RNA and primer mixture. The solution was incubated for 1 hour at 40° C., followed by 70° C. incubation for 15 minutes to deactivate SuperScript and chill for 2 minutes. 1 µl of RNase H (2 U) was added to the reaction mixture and incubated at 37° C. for 2 minutes.

Cloning and Sequencing of AaeIAP1 from *Aedes aegypti*

Cloning the full length AaeIAP1 gene was carried out using Generacer kit (Invitrogen) as described by the manufacturer. The AaeIAP1 gene having Genbank accession number AY559037 was cloned from *Ae. Aegypti*. Sequence analysis of the gene using SMART (Schultz et al. 1998) program indicates that all six insect IAP1s contain two BIR domains and a C-terminal RING domain, and that the two BIR domains and the RING motif are signature structures for insect IAP1. BIR domains are well-known for their ability to bind and inhibit caspases and mediate protein-protein interaction. The RING domain is a signature motif for proteins that possess ubiquitin ligase activity.

The first strand cDNAs were synthesized with AMV reverse transcriptase using *Ae. aegypti* mRNAs as templates. Sense primer IAPF (5'-ATGGCTGGAGTTATGATGGC-3' (SEQ. ID. NO 12) corresponding to the nucleotides 1-20) was designed based on the sequence of the IAP gene from *Ae. aegypti*. The GeneRacer 3' primer provided by the kit was used as antisense primer for PCR. The PCR reaction was carried out in a thermocycler (MWG Biotech, High Point, N.C.) at 94° C. (2 min) with the subsequent 35 cycles at 94° C. (1 min), 60° C. (1 min) and 72° C. (2 min) followed by a final extension at 72° C. for 20 minutes. The PCR amplification products were gel purified (QIAGEN, Valencia, Calif.), cloned into PCR2.1 vector provided by the TOPO-TA cloning kits (Invitrogen, Carlsbad, Calif.), and sequenced by automated sequencing (DNA Sequencing Facility, University of Florida). Sequence analyses of the AaeIAP1 clones were repeated at least three times with different preparations of mRNAs. Three TA clones from each replication were verified by sequencing.

Construction of AeIAP1 dsRNA Products and Cun85 dsRNA Control

Four double-stranded RNA products were made using the MEGAscript® RNAi Kit (Ambion, Austin, Tex.). The dsRNA product (dsRNA-IAP1-B) was designed to cover the N-terminal portion of AaeIAP1 and part of its first BIR domain. It was constructed by amplifying plasmid DNA containing a cloned 210 bp fragment with the T7-IAP-183F/T7-IAP-385R primers (Table 1) that had T7 promoter sequence (5'-TAATACGACTCACTATAGGG-3' (SEQ. ID. NO 13)) added to the 5' end of each primer. The resulting template was then transcribed at 37° C. for 16 hours using T7 RNA polymerase in the presence of ATP (75 mM), UTP (75 mM), GTP (75 mM), and CTP (75 mM) following the manufacturer's protocol (Ambion, Austin, Tex.). Sixteen hours post transcription, reaction was incubated at 75° C. for 5 min then left at room temperature to maximize double strand RNA yield. DNase I and RNase were then added to the reaction followed by incubation at 37° C. for 60 min to remove DNA template and ssRNA. Binding buffer and ethanol were then added to the dsRNA reaction to assemble the dsRNA binding mix. The binding mix was then passed to a filter cartridge to remove proteins, free nucleotides, and nucleic acid degradation products from the dsRNA. The filter cartridge was then washed twice with wash solution. The dsRNA was then recovered by eluting with preheated 75° C. nuclease-free H₂O.

TABLE 1

Primer name and sequence used for the preparation of DNA template used for AaeIAP1 dsRNA synthesis

| Primer Name | Primer Sequence |
|---|---|
| T7-IAP1-185F (SEQ. ID. 1) | TAATACGACTCACTATAGGGGGCTGGAGT TATGATGGCTC |
| T7-IAP1-395R (SEQ. ID. 2) | TAATACGACTCACTATAGGGTGGCCCCAC GTAGTAG |
| T7-IAP1-375F (SEQ. ID. 3) | TAATACGACTCACTATAGGGGTTTCTACT ACGTGGGGCCA |
| T7-IAP1-931R (SEQ. ID. 4) | TAATACGACTCACTATAGGGCAGCTTCCC AGTCTTTGAGG |
| T7-IAP1-911F (SEQ. ID. 5) | TAATACGACTCACTATAGGGCCTCAAAG ACTGGGAAGCTG |
| T7-IAP1-1347R (SEQ. ID. 6) | TAATACGACTCACTATAGGGGACACAAC GGACACTTGGTG |
| T7-Cun85-2020F (SEQ. ID. 7) | TAATACGACTCACTATAGGGAAATTCG CAAGCTTTAC |
| T7-Cun85-2640R (SEQ. ID. 8) | TAATACGACTCACTATAGGGTGAGCGCA GATTGTGGAAG |

The dsRNA product (dsRNA-IAP1-C) was designed to produce the middle portion of AaeIAP1 which contains the second BIR domain and the rest of the first BIR domain. It was constructed by amplifying plasmid DNA containing a cloned ~556 bp fragment AaeIAP1 with the T7-IAP-375F/T7-IAP-931R primer set (Table 1). The resulting template was then transcribed for 16 hours. The dsRNA product (dsRNA-IAP1-D) contained the rest of the AaeIAP1 which contains a C-terminal RING domain. Plasmid DNA containing a cloned ~436 bp fragment of AaeIAP1 was amplified using T7-IAP-911F/T7-IAP-1347R primer set (Table 1). The resulting template was transcribed for 16 hours. Another dsRNA product was designed to produce a non-silencing dsRNA control using Cun85 from *Culex nigripalpus* baculovirus (CuniNPV) as template (Afonso et al., 2001). Primer set T7-Cun85-2020F/T7-Cun85-2640R (Table 1) was designed based on the sequence of the Cun85 gene published in the genome of CuniNPV (Genbank accession no: AF403738). The resulting template was then transcribed for 16 hours. DNA and ssRNA were removed and the dsRNA products were then purified via nuclease digestion following the manufacturer's protocol (Ambion, Austin, Tex.). The concentrations of the resulting dsRNA products were then measured. The concentration of dsRNA-IAP-B was 0.672 µg/µl. The concentration of dsRNA-IAP-C was 0.752 µg/µl. The concentration of dsRNA-IAP-D was 0.48 µg/µl. The concentration of dsRNA-Cun85-A was 0.784 µg/µl.

Sequence analysis using SMART program (Schultz et al. 1998) indicates that AaeIAP1 encodes a 401 amino acid protein containing two conserved BIR domains and a RING domain (FIG. 1). The first BIR domain was predicted to be 71 amino acid in length (39aa to 109aa) and the second BIR domain was 72 amino acid in length (198aa to 269aa). The C-terminal RING domain spanned from 354 amino acid to 388 amino acid in length. To confirm that AaeIAP1 was structurally similar to the other insect IAPs, the SMART program was used to compare the conserved domains among the insect IAP1s of DIAP1 from *Drosophila melanogaster*, TnIAP1 from *Trichoplusia ni*, SfIAP1 from *Spodoptera frugiperda*, BmIAP from *Bombyx mori*, and AtIAP1 from *Ae. Triseriatus*. As shown in FIG. 1, all six insect IAP1s contained two BIR domains and one C-terminal RING domain, indicating that two BIR domains and the C-terminal RING domain are signature structures for insect IAP1. Sequence analysis reveals the domain structures of the three IAP1s (AaeIAP1, AtIAP1, and DIAP1) from Diptera are very similar to each other. There is only slight difference (2aa length difference and 2aa domain shift) between the two mosquito IAP1s, AaeIAP1 and AtIAP1. The three Lepidoptera IAP1s (TnIAP1, SfIAP1, and BmIAP1) share similar domain structures. No or slight differences were observed between the cabbage looper TnIAP1 and fall armyworm SfIAP1. There is no difference in the first BIR domain between TnIAP1 and SfIAP1. Only one amino acid shift was observed in the second BIR domain and a two amino acid shift in the RING domain. The silkworm BmIAP1 domain structure was not as similar to SfIAP1 as TnIAP1, which is 31 to 33aa shorter in length when compared to SfIAP1 and TnIAP1, respectively.

Figure 2:
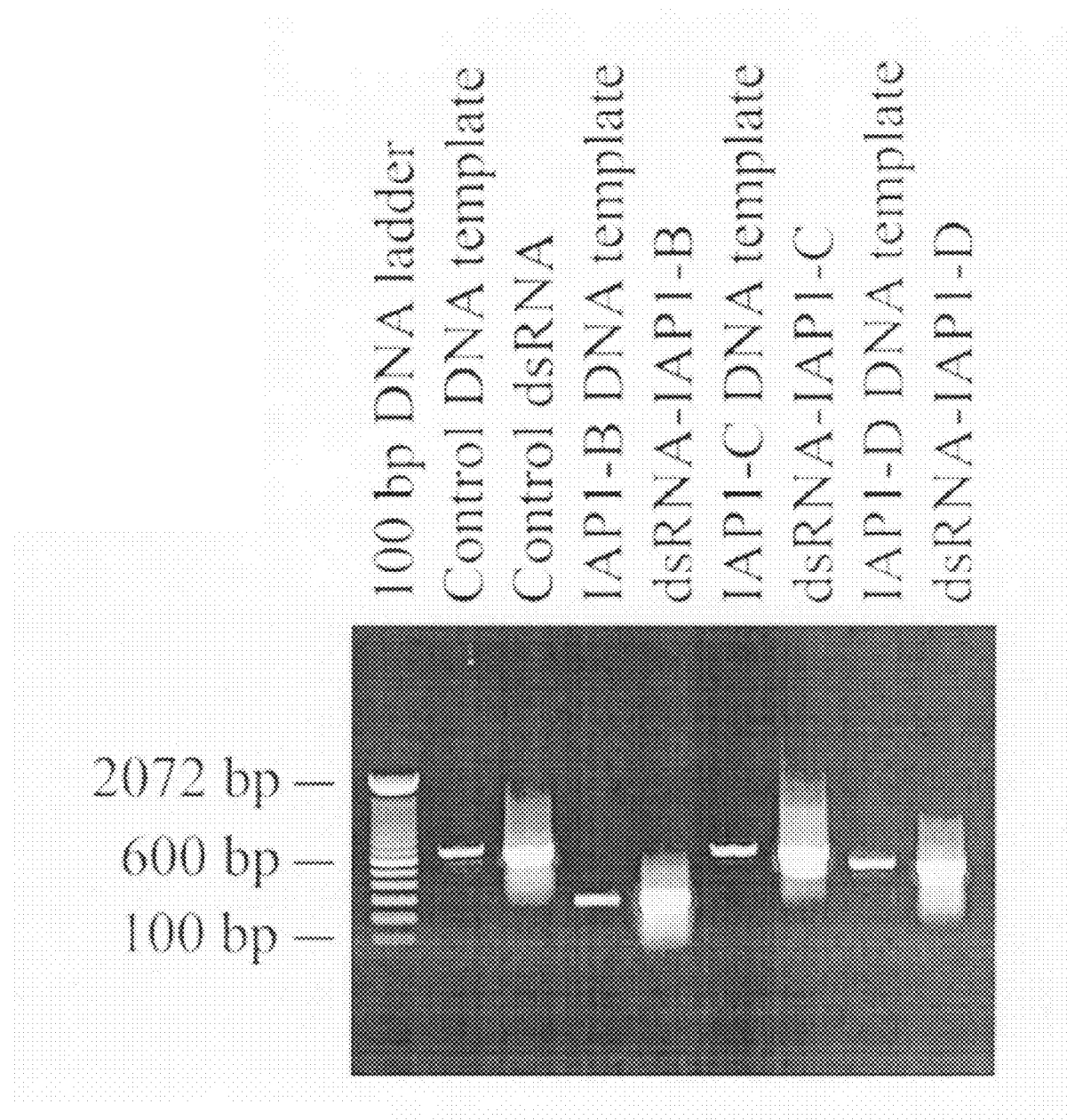
FIG. 2 is a picture of an agarose gel (1%) electrophoresis of dsRNA synthesized. The amount of the 100 bp DNA marker was 0.5 μg. The amount of the DNA templates loaded in the gel was 0.5 μg. The amount of the control dsRNA product Cun85 was 2.3 μg. The amount of the AaeIAP1 dsRNA products loaded in the gels was 2.01 μg, 2.25 μg, and 1.92 μg, respectively.

The quality of the non-silencing dsRNA control Cun85 and the three AaeIAP1 dsRNA products (dsRNA-IAP1-B, dsRNA-IAP1-C, and dsRNA-IAP1-D) was analyzed by 1% agarose gel electrophoresis along with their DNA templates (FIG. 2). The expected size for the non-silencing dsRNA control Cun85 was 621 bp. The expected sizes for the three silencing AaeIAP1 dsRNA products (dsRNA-IAP1-B, dsRNA-IAP1-C, and dsRNA-IAP1-D) were 211 bp, 557 bp, and 437 bp, respectively. As shown in FIG. 2, all four dsRNA products showed up single sharp bands, indicating that dsRNA products were synthesized successfully. The concentrations for the four dsRNA products were and 0.784 µg/µl, 0.672 µg/µl, 0.752 µg/µl, and 0.48 µg/µl, respectively. FIG. 2 shows dsRNA products migrated at about the same speed as the same length DNA templates.

Cell Culture and Transfection

The *Ae. aegypti* cell line, Aag-2, was maintained in Schneider's insect medium (Sigma Aldrich, St. Louis, Mo.) supplemented with 10% fetal bovine serum (FBS) (Invitrogen, San Diego, Calif.). Transfection experiments were performed in 60 mm cell culture dishes using Trans-IT Si-QUEST transfection reagent (Mirus Bio Corporation, Madison, Wis.) following the manufacturer's instructions. Cells were incubated at 26±0.5° C. until they reached ~90% confluency (approximately 24 hours). Spent medium was removed and replaced with 1.5 ml of fresh Schneider medium containing 10% FBS. Typically, a final concentration of 25 nM of dsRNA product was added to each dish. Following transfection, the cells were incubated for an additional 6 h at 26±0.5° C. and plated in 96-well plates (for cell viability assay) and 6-well plates (for DNA fragmentation assay and RNA extraction).

Example 1

Cell Documentation and DNA Fragmentation Assay

The Aag-2 cells transfected with or without dsRNA products were seeded on 6-well plates and incubated at 26±0.5° C. Twenty four hours post-transfection, cells were photographed with a Nikon inverted microscope (Nikon, Lewisville, Tex.). Cells were then harvested for DNA fragmentation assay. DNA fragmentation is a hallmark of cells undergoing apoptosis (Darzynkiewicz et al. 2006). The DNA fragmentation assay was performed with a well established method by those having ordinary skill in the art (Masuda et al. 2004). Aag-2 cells transfected with or without double-stranded RNA were collected by centrifugation and washed with Dulbecco's phosphate-buffered saline (PBS) three times. The washed cell pellets were saved at −80° C. and were suspended in cell lysis buffer (10 mM Tris-HCl (pH 8.0), 10 mM EDTA, 0.5% SDS) containing 0.1% RNase A and incubated for 60 min at 50° C. The cell lysate was incubated for an additional 60 min at 50° C. in the presence of 1 mg/ml proteinase K, and the resulting preparation of DNA was analyzed by gel electrophoresis on a 1% agarose gel in Tris acetate buffer (40 mM Tris acetate, 1 mM EDTA). After electrophoresis, DNA was visualized by staining with ethidium bromide. Gels were photographed with a digital camera (Olympus, Melville, N.Y.) and band intensities were analyzed using Scion Image program (Scion, Frederick, Md.). The extent of DNA fragmentation was judged by the ratio of the amount of unfragmented DNA to the total amount of DNA. The Student's t-test was used to compare the extents of unfragmented DNA among different samples with a criterion of $P \leq 0.05$. 2.6.

Figure 3:
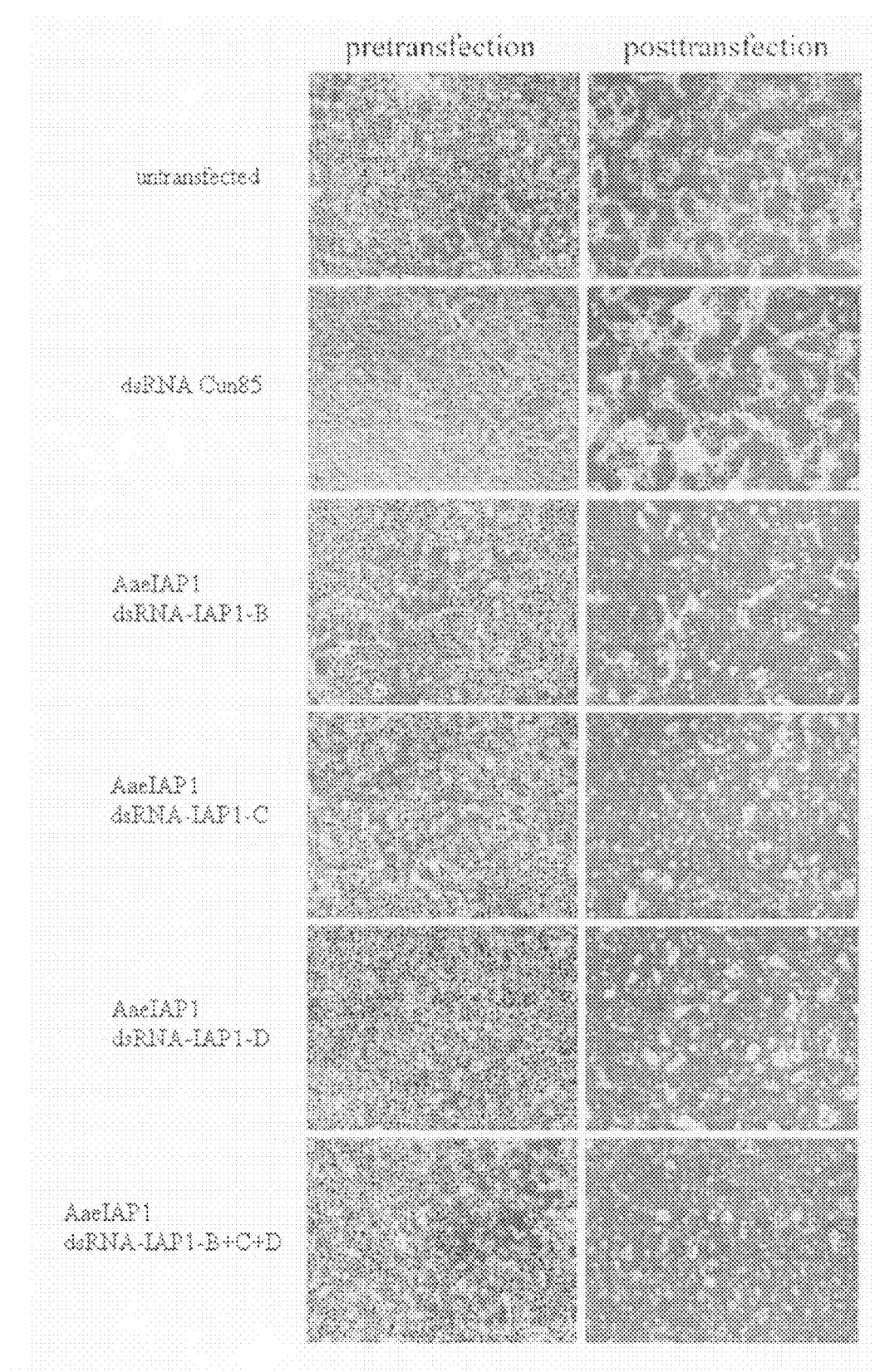
FIG. 3 is a picture of dsRNA treatment on Aag-2 cells. Aag-2 cells were plated on 60 mm cell culture dishes 12 hours before the transfection. When cells reached ~90% confluency, pictures were taken with a digital camera and cells were then transfected with 25 nM of dsRNA products. Eight hours post-transfection, cells from one 60 mm cell culture dish were split to 60 wells of a 96-well plate for MTT assay. The remained cells were plated to two wells of a 6-well plate. Cells in the 6-well plates were documented under an inverted microscope 24 h post-transfection. The cells in the 6-well plates were ~40% confluent. The experiments were repeated three times. UT: untransfected; CK: control dsRNA Cun85; B: AaeIAP1 dsRNA-IAP1-B; C: AaeIAP1 dsRNA-IAP1-C; D: AaeIAP1 dsRNA-IAP1-D; BCD: AaeIAP1 dsRNA-IAP1-B+dsRNA-IAP1-C+dsRNA-IAP1-D

Twenty-four hours post-transfection, the majority of the Aag-2 cells treated with AaeIAP1 dsRNA products detached from the cell culture plates (FIG. 3). In contrast, Aag-2 cells transfected without or with the non-silencing dsRNA Cun85 remained attached to the cell culture plates (FIG. 3). Detachment from the cell culture substrata is one of the characteristic changes of apoptotic cells (Suzuki T. et al., 2001. *Free Radic. Biol. Med.*, 31:615-623).

Figure 4:
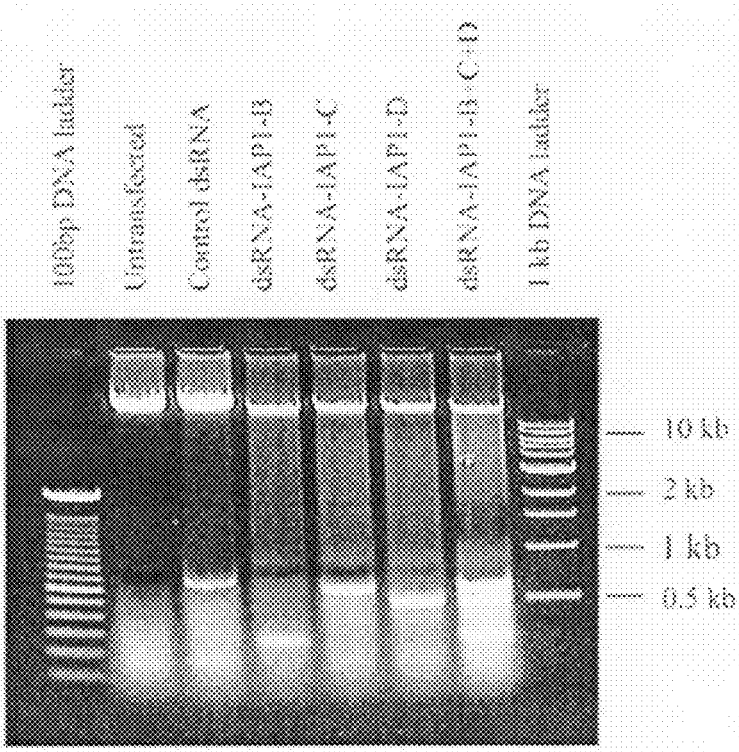
FIG. 4A is a picture of DNA fragmentation by 1% agarose gel electrophoresis of 100 bp DNA ladder, untransfected sample, control dsRNA, dsRNA-IAP1-B, dsRNA-IAP1-C, dsRNA-IAP1-D, and dsRNA-IAP1-B+C+D.
FIG. 4B is an analysis of unfragmented DNA intensities with the Scion image program. The data are presented as means±S.D. of the results of three independent experiments. Different letters indicate significant difference ($P \leq 0.05$) among the samples.
Figure 4:
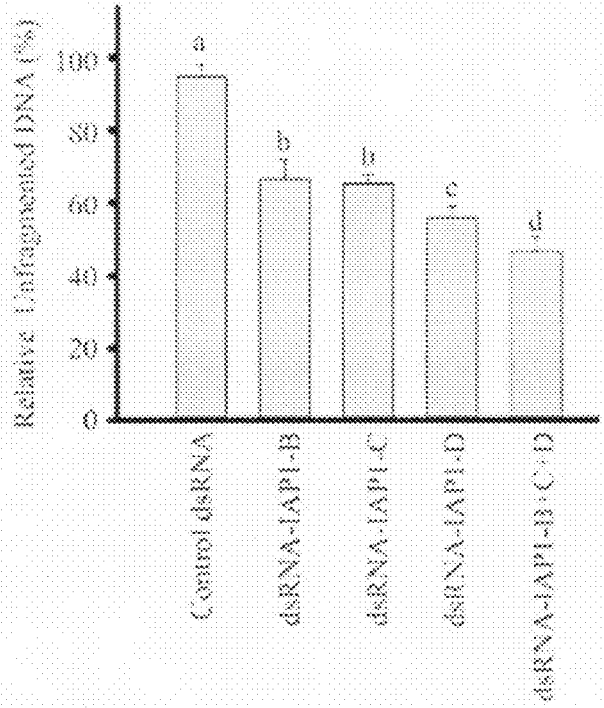

To further confirm the apoptotic effect of AaeIAP1 dsRNA products on Aag-2 cells, DNA fragmentation assays were performed. The effect of AaeIAP1 dsRNA products on the induction of apoptosis were shown in FIGS. 4 A and B. The extent of DNA fragmentation was significantly higher in Aag2-cells treated with AaeIAP1 dsRNA-IAP1-D and the combination of the three dsRNA products (dsRNA-IAP1-B, dsRNA-IAP1-C, and dsRNA-IAP1-D). In contrast, DNA fragmentation effects were not observed in either the Aag-2 cells transfected without any dsRNA products or with a non-silencing dsRNA product Cun85 (from CuniNPV virus).

Example 2

Cell Viability Assay

Figure 5:
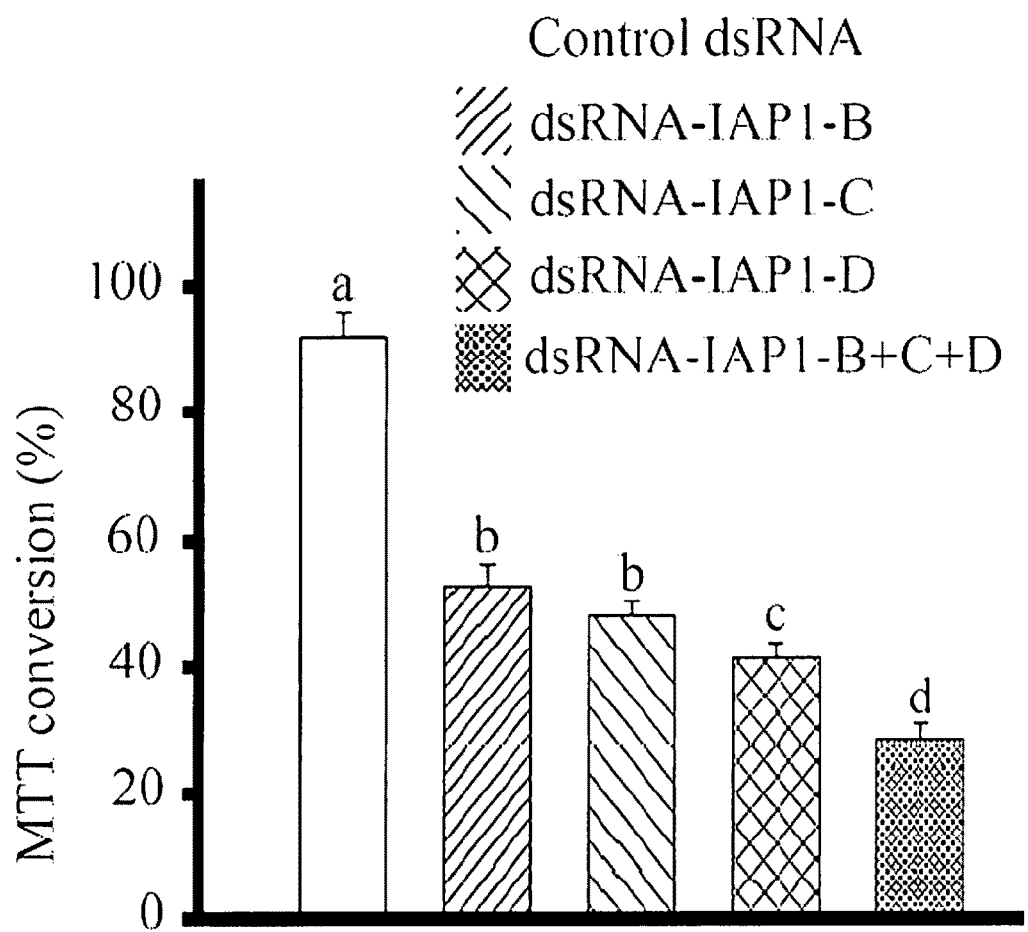
FIG. 5 is graph depicting the effect of dsRNA products on cell viability. Twenty-four hours after transfecting Aag-2 cells with 25 nM dsRNA products, methyl thiazol tetrazolium (MTT) assay was performed. The data are presented as means±S.D. of the results of three independent experiments. Different letters indicate significant difference ($P \leq 0.05$) among the samples.

To verify the apoptotic effects of AaeIAP1 dsRNA products on Aag-2 cells, cell viability assays were performed. As shown in FIG. 3, little difference was observed between cells treated with or without non-silencing Cun85 dsRNA product. However, when Aag2-cells were treated with AaeIAP1 dsRNA products, cell viability decreased significantly (FIG. 5). Consistent with DNA fragmentation, the effect of dsRNA-IAP1-D and the combination of the three AaeIAP1 dsRNA products (dsRNA-IAP1-B, dsRNA-IAP1-C, and dsRNA-IAP1-D) on Aag-2 cell viability were greater than that by AaeIAP1 dsRNA-IAP1-B or dsRNA-IAP1-C (FIG. 5). The conversion of methyl thiazol tetrazolium (MTT) to a colored formazan has been used extensively as a marker for cell viability since the early 1980's (Mosmann T. et al., 1983. *J. Immunol. Methods*, 65:55-63; Niering P. et al., 2005. *Toxicol Appl. Pharmacol.*, 209:114-112). The cell viability assay was performed using a well established protocol (Spee B. et al., 2006. *Mol. Cancer*, 5:34). Briefly, the Aag-2 cells transfected with or without dsRNA products were seeded on 96-well plates at a density of 5×10³ cells/well in Schneider's insect medium 6 hours post-transfection. The cells were then incubated at 26±0.5° C. Twenty-four hours post-transfection, methyl thiazol tetrazolium (Sigma, St. Louis, Mo.) was added to the 96-wells at 0.25 mg/ml for 4 hours at 26±0.5° C. and the reaction was terminated by the addition of 0.4N HCl in 100% isopropanol. The amount of formazan product was measured at 560 nm on a microplate reader.

Example 3

RNA Extraction and Multiplex Reverse Transcriptase-PCR

Figure 6A:
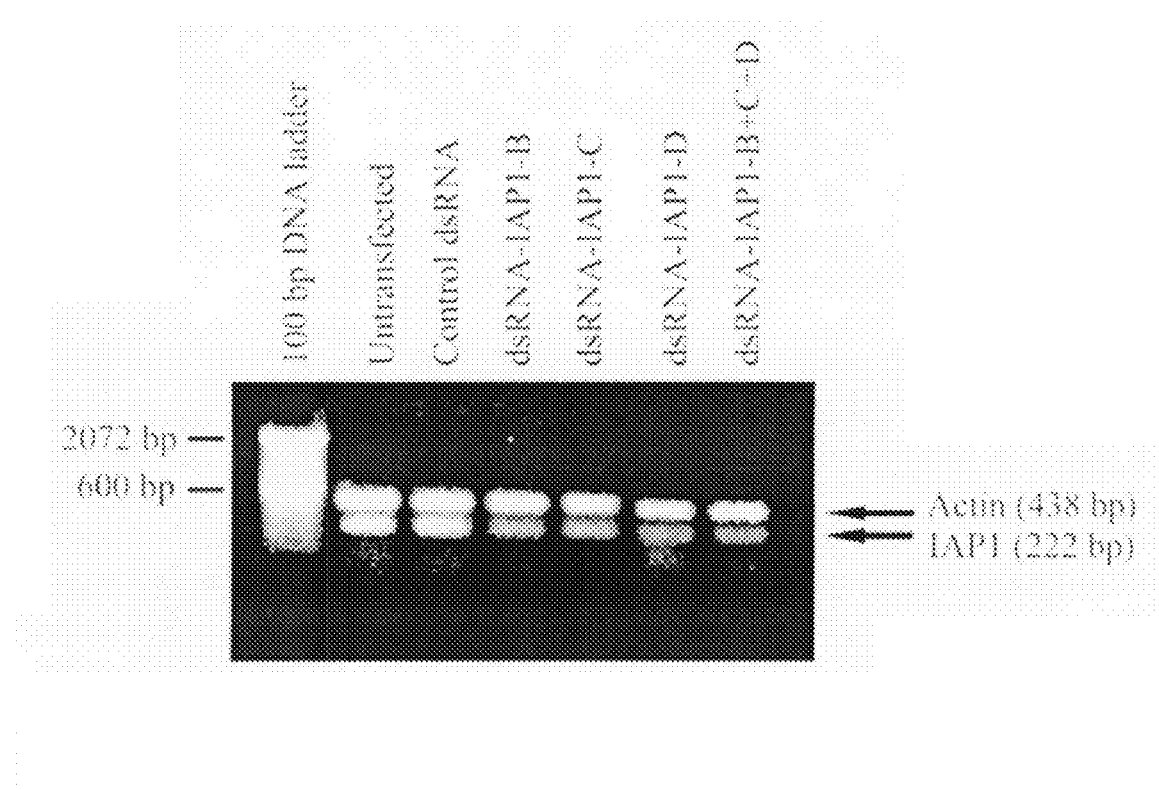
FIG. 6A is a picture of 1% agarose gel electrophoresis of AaeIAP1 gene expression of 100 bp DNA ladder, untransfected sample, control dsRNA, dsRNA-IAP1-B, dsRNA-IAP1-C, dsRNA-IAP1-D, and dsRNA-IAP1-B+C+D.
Figure 6B:
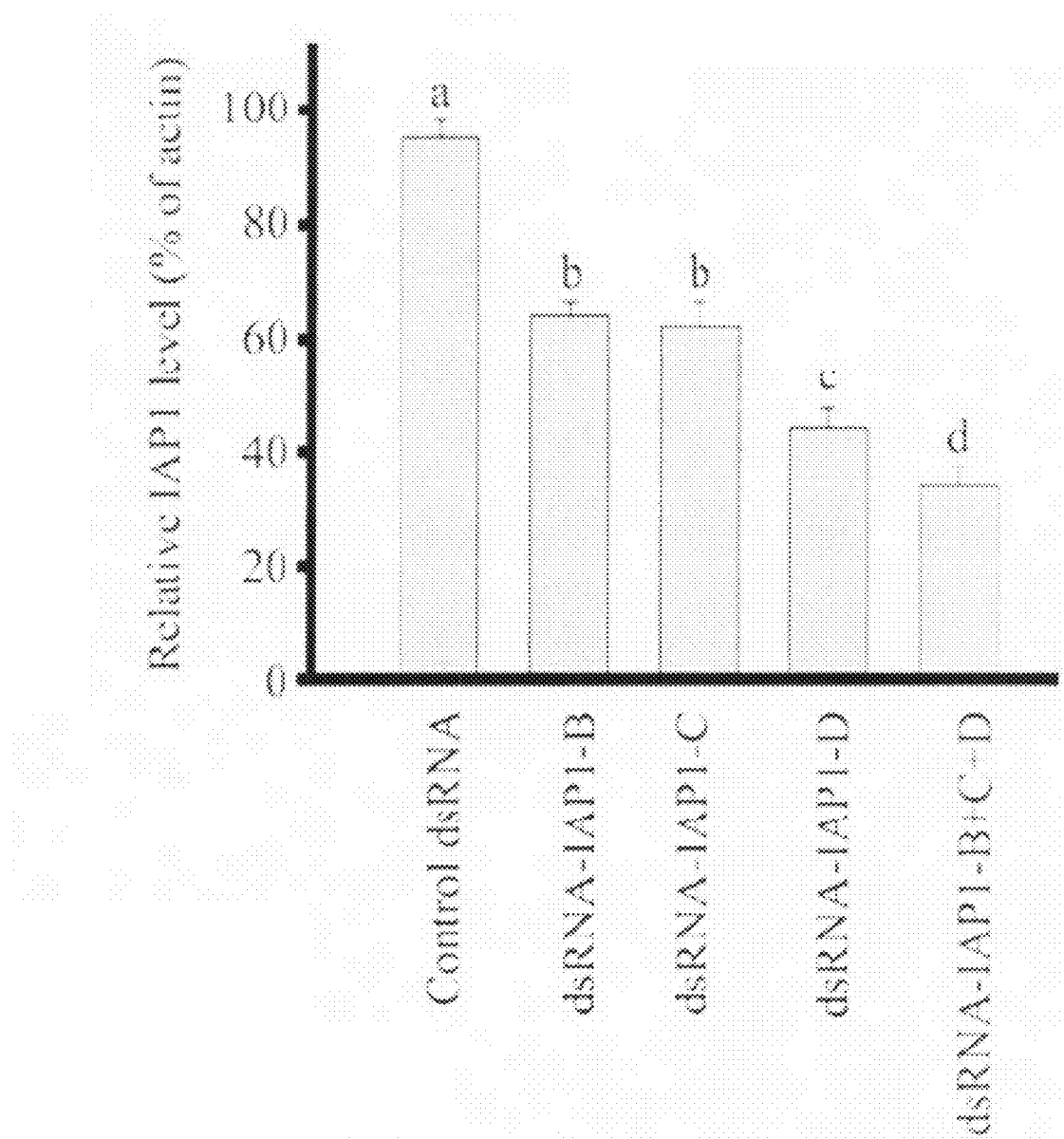
FIG. 6B a graphical depiction of AaeIAP1 expression level with the Scion image program. The data are presented as means±S.D. of the results of three independent experiments. Different letters indicate significant difference ($P \leq 0.05$) among the samples.

Since AaeIAP1 dsRNA products induced apoptosis and reduced cell viability in Aag-2 cell lines, gene silencing effects caused by the treatments of AaeIAP1 dsRNA products were evaluated through multiplex RT-PCR and real-time quantitative PCR using actin as an internal control. As shown in FIG. 6, treatment of Aag-2 cells with AaeIAP1 dsRNA products significantly suppressed the expression of AaeIAP1. In contrast, little or no significant AaeIAP1 gene suppression was observed in cells treated with or without non-silencing Cun85 dsRNA product (FIGS. 6 A and B). Consistent with the results of DNA fragmentation and cell viabilities, AaeIAP1 expression was more suppressed by dsRNA-IAP1-D and the combination of the three AaeIAP1 dsRNA products (dsRNA-IAP1-B, dsRNA-IAP1-C, and dsRNA-IAP1-D) than by dsRNA-IAP1-B and dsRNA-IAP1-C (FIGS. 6 A and B).

Twenty-four hours post-transfection, Aag-2 cells were collected by centrifugation and washed with Dulbecco's phosphate-buffered saline three times and the cell pellets were saved in −80° C. for subsequent RNA extraction. Total RNA was prepared and reverse transcribed as described supra. Gene expression was analyzed using multiplex RT-PCR. The cDNA was then amplified in a PCR multiplex reaction using sense primer IAP-911F (SEQ. ID. 5) and antisense primer IAP-1133R (SEQ. ID. 9) plus the actin primer set Actin-152F 5' (SEQ. ID. 10) and Actin-590R 5' (SEQ. ID 11). *Aedes aegypti* actin gene (GenBank accession no DQ440059) was selected as an internal control in all reactions. The multiplex PCR reaction mixture of 50 μl contained 1 μl of cDNA, 1× of PCR reaction buffer (10 mM Tris-HCl pH 9.0, 50 mM KCl, 0.1% Triton® X-100), 0.25 μM of primer pairs, 2 mM MgCl$_2$, 0.2 mM dNTPs and 1.25 units of Taq DNA polymerase (Promega, Madison, Wis.). Amplification was conducted in an MWG biotech thermal cycler under the following conditions: initial denaturation at 94° C. (2 min) with the subsequent 35 cycles at 94° C. (45 s), 55° C. (45 s) and 72° C. (45 s) followed by a final extension at 72° C. for 5 minutes. PCR products were visualized by 2.0% agarose gel electrophoresis in TAE buffer and ethidium bromide staining. Gels were documented and band intensities were analyzed using Scion Image program (Scion, Frederick, Md.).

Example 4

Real-Time Quantitative PCR

Quantitative PCR was carried out in a 7300 real-time PCR system (Applied Biosystems, Foster City, Calif.) using Platinum SYBR green qPCR SuperMix (Invitrogen, Carlsbad, Calif.). Master cDNA and SYBR green SuperMix were prepared for each cDNA sample for four reactions, two of the reactions were for IAP1 primer set and the other two reactions were for actin primer set to eliminate template amount difference in each reaction. Normalized with the actin level, the percentages of IAP1 mRNA levels were calculated over that in untransfected cells. The primers for real-time PCR were utilized as described supra.

Figure 7:
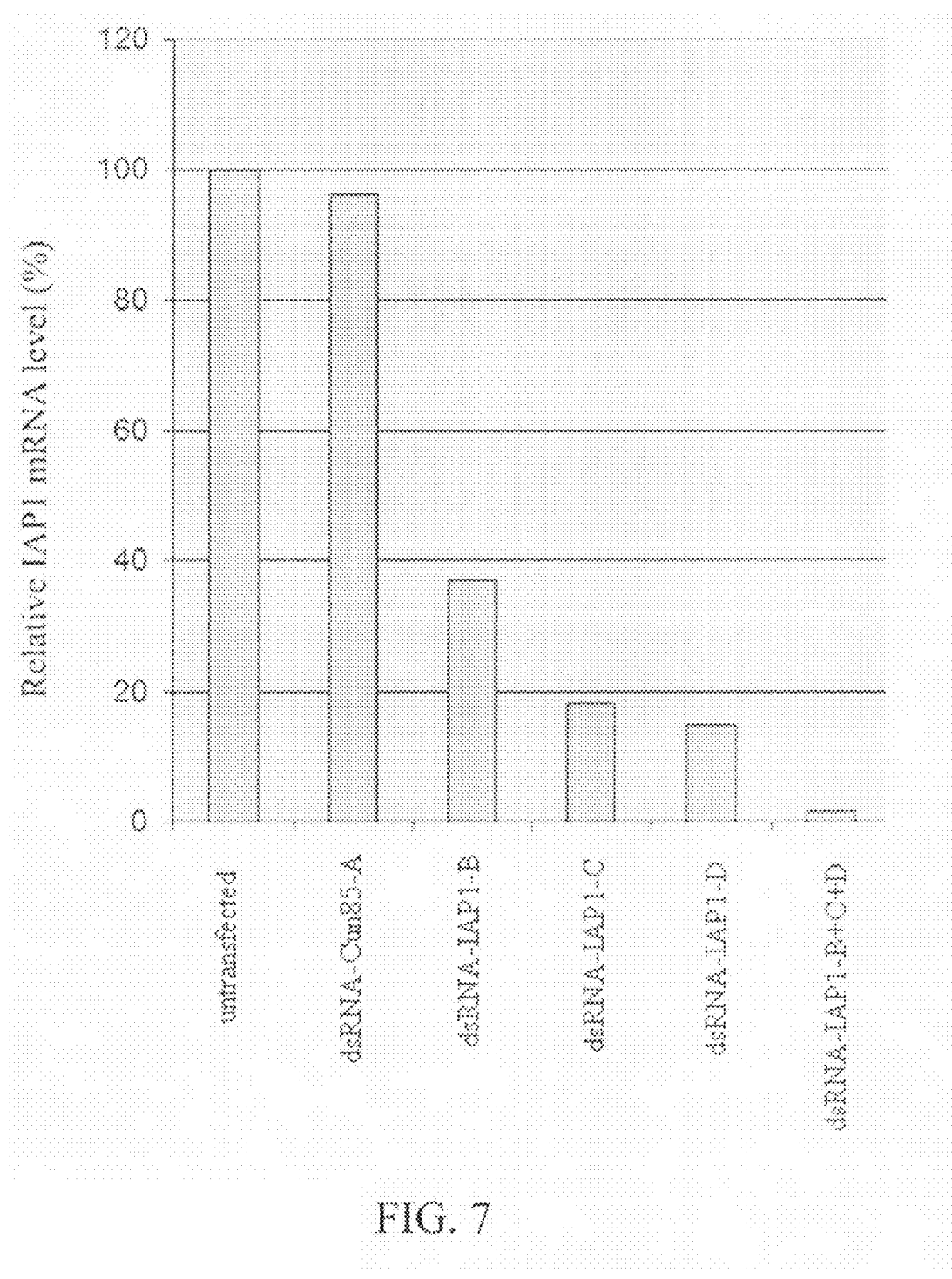
FIG. 7 a graphical depiction of AaeIAP1 mRNA levels as determined by real-time quantitative PCR. The AaeIAP1 mRNA levels are in percentage of AaeIAP1 mRNA in each treatment over that in untransfected cell after being normalized with actin mRNA.

Relative quantitative PCR revealed the transcript levels of AaeIAP1 gene at 24 hour post-transfection were decreased about 22-fold and 273-fold in cells transfected with ds-RNA-IAP1-D and dsRNA-IAP1-B+C+D (Table 2). In contrast, AaeIAP1 transcript levels were not significantly changed in cells transfected with non-targeting Cun85-A dsRNA (FIG. 7).

TABLE 2

Quantitative real-time PCR results

| cDNA + Primer | Ct1 | Ct2 | Average Ct. | Δ Ct | Fold (Actin/IAP1) | IAP1 mRNA (% of UT) |
|---|---|---|---|---|---|---|
| UT + IAP | 19.36 | 19.27 | 19.315 | 1.95 | 3.86 | 100 |
| UT + Actin | 17 | 17.73 | 17.365 | | | |
| Cun85 + IAP | 20.02 | 20.26 | 20.14 | 2.005 | 4.01 | 96.3 |
| Cun85 + Actin | 18.2 | 18.07 | 18.135 | | | |
| IAP − B + IAP | 21.85 | 21.71 | 21.78 | 3.37 | 10.34 | 37.3 |
| IAP − B + Actin | 18.45 | 18.37 | 18.41 | | | |
| IAP − C + IAP | 22.6 | 23.07 | 22.835 | 4.405 | 21.19 | 18.2 |
| IAP − C + Actin | 18.44 | 18.42 | 18.43 | | | |
| IAP − D + IAP | 22.78 | 22.6 | 22.69 | 4.68 | 25.63 | 15.1 |
| IAP − D + Actin | 17.92 | 18.1 | 18.01 | | | |
| IAP − BCD + IAP | 27.34 | 27.14 | 27.24 | 8.115 | 277.24 | 1.4 |
| IAP − BCD + Actin | 19.03 | 19.22 | 19.125 | | | |

Example 5

Adult Bioassays

To determine whether dsRNA-IAP-B, IAP-C, IAP-D and IAP-B+C+D products were able to kill female adults of *Aedes aegypti* directly, each dsRNA product was diluted in acetone or in siQuest transfection reagent and topically applied to individual mosquitoes. Topical application bioassay results revealed that dsRNA-IAP-B, IAP-C, IAP-D and IAP-B+C+D products were able to kill female adults of *Aedes aegypti*, either in the presence of acetone or siQUEST (Table 3 and Table 4).

Prior to topical application, 5-7 day-old females were briefly anaesthetized for 30 seconds with carbon dioxide and placed on a 4° C. chill table (BioQuip Products, Rancho Dominguez, Calif.). A droplet of 0.5 μl of dsRNA-IAP solution was applied to the dorsal thorax using a 700 series syringe and a PB 600 repeating dispenser (Hamilton, Reno, Nev.). Acetone alone was also applied to the dorsal thorax of *Aedes aegypti* as a control treatment. After treatment, mosquitoes were kept in plastic cups and supplied with 10% sucrose solution and mortality was recorded in indicated time points. Temperature and humidity were maintained at 26° C. and 80% RH, respectively. Every bioassay was conducted at 27° C. and 80% RH.

TABLE 3

Insecticidal activities of dsRNA-IAP1 products against female adults of *Aedes aegypti* by topical application using acetone as a carrier

| Solution | Vol. Ratio of Carrier to dsRNA | Died/Total | Percent Mortality |
|---|---|---|---|
| 3 hours | | | |
| Acetone | — | 0/30 | 0% |
| Acetone + dsRNA IAP-B | 3:1 | 2/19 | 11% |
| Acetone + dsRNA IAP-C | 3:1 | 1/30 | 3% |
| Acetone + dsRNA IAP-D | 3:1 | 3/29 | 10% |
| Acetone + dsRNA IAP-B + C + D | 3:1:1:1 | 4/28 | 14% |
| 6 hours | | | |
| Acetone | — | 0/30 | 0% |
| Acetone + dsRNA IAP-B | 3:1 | 2/19 | 11% |
| Acetone + dsRNA IAP-C | 3:1 | 2/30 | 7% |
| Acetone + dsRNA IAP-D | 3:1 | 4/29 | 14% |
| Acetone + dsRNA IAP-B + C + D | 3:1:1:1 | 7/28 | 25% |
| 12 hours | | | |
| Acetone | — | 0/30 | 0% |
| Acetone + dsRNA IAP-B | 3:1 | 2/19 | 11% |
| Acetone + dsRNA IAP-C | 3:1 | 3/30 | 10% |
| Acetone + dsRNA IAP-D | 3:1 | 4/29 | 14% |
| Acetone + dsRNA IAP-B + C + D | 3:1:1:1 | 9/28 | 32% |
| 18 hours | | | |
| Acetone | — | 0/30 | 0% |
| Acetone + dsRNA IAP-B | 3:1 | 2/19 | 11% |
| Acetone + dsRNA IAP-C | 3:1 | 4/30 | 13% |
| Acetone + dsRNA IAP-D | 3:1 | 5/29 | 17% |
| Acetone + dsRNA IAP-B + C + D | 3:1:1:1 | 11/28 | 39% |
| 24 hours | | | |
| Acetone | — | 0/30 | 0% |
| Acetone + dsRNA IAP-B | 3:1 | 3/19 | 16% |
| Acetone + dsRNA IAP-C | 3:1 | 4/30 | 13% |
| Acetone + dsRNA IAP-D | 3:1 | 5/29 | 17% |
| Acetone + dsRNA IAP-B + C + D | 3:1:1:1 | 13/28 | 46% |
| 48 hours | | | |
| Acetone | — | 2/30 | 7% |
| Acetone + dsRNA IAP-B | 3:1 | 4/19 | 21% |
| Acetone + dsRNA IAP-C | 3:1 | 7/30 | 23% |
| Acetone + dsRNA IAP-D | 3:1 | 7/29 | 24% |
| Acetone + dsRNA IAP-B + C + D | 3:1:1:1 | 15/28 | 54% |

TABLE 4

Insecticidal activities of dsRNA-IAP1 products against female adults of *Aedes aegypti* by topical application using siQuest transfection reagent as a carrier

| Solution | Vol. Ratio of Carrier to dsRNA | Died/Total | Percent Mortality |
|---|---|---|---|
| 3 hours post application | | | |
| siQuest | — | 0/25 | 0% |
| siQuest + dsRNA IAP-B | 3:1 | 2/28 | 7% |
| siQuest + dsRNA IAP-C | 3:1 | 2/28 | 7% |
| siQuest + dsRNA IAP-D | 3:1 | 8/25 | 32% |
| siQuest + dsRNA IAP-B + C + D | 3:1:1:1 | 1/30 | 3% |
| 6 hours post application | | | |
| siQuest | — | 1/25 | 4% |
| siQuest + dsRNA IAP-B | 3:1 | 2/28 | 7% |
| siQuest + dsRNA IAP-C | 3:1 | 2/28 | 7% |
| siQuest + dsRNA IAP-D | 3:1 | 8/25 | 32% |
| siQuest + dsRNA IAP-B + C + D | 3:1:1:1 | 2/30 | 7% |
| 12 hours post application | | | |
| siQuest | — | 1/25 | 4% |
| siQuest + dsRNA IAP-B | 3:1 | 4/28 | 14% |
| siQuest + dsRNA IAP-C | 3:1 | 3/28 | 11% |
| siQuest + dsRNA IAP-D | 3:1 | 8/25 | 32% |
| siQuest + dsRNA IAP-B + C + D | 3:1:1:1 | 5/30 | 17% |
| 18 hours post application | | | |
| siQuest | — | 1/25 | 4% |
| siQuest + dsRNA IAP-B | 3:1 | 5/28 | 18% |
| siQuest + dsRNA IAP-C | 3:1 | 3/28 | 11% |
| siQuest + dsRNA IAP-D | 3:1 | 11/25 | 44% |
| siQuest + dsRNA IAP-B + C + D | 3:1:1:1 | 7/30 | 23% |
| 24 hours post application | | | |
| siQuest | — | 1/25 | 4% |
| siQuest + dsRNA IAP-B | 3:1 | 9/28 | 32% |
| siQuest + dsRNA IAP-C | 3:1 | 3/28 | 11% |
| siQuest + dsRNA IAP-D | 3:1 | 13/25 | 52% |
| siQuest + dsRNA IAP-B + C + D | 3:1:1:1 | 10/30 | 33% |
| 48 hours post application | | | |
| siQuest | — | 2/25 | 8% |
| siQuest + dsRNA IAP-B | 3:1 | 9/28 | 32% |
| siQuest + dsRNA IAP-C | 3:1 | 10/28 | 36% |
| siQuest + dsRNA IAP-D | 3:1 | 18/25 | 72% |
| siQuest + dsRNA IAP-B + C + D | 3:1:1:1 | 10/30 | 33% |

TABLE 5

Insecticidal activities of dsRNA-IAP-B product against female adults of *Aedes aegypti* by topical application using acetone as a carrier

| Solution | Vol. Ratio of Acetone to dsRNA | Died/Total | Percent Mortality |
|---|---|---|---|
| 4 hours post application | | | |
| Acetone | 1:0 | 1/30 | 3% |
| Acetone + dsRNA IAP-B | 1:1 | 0/28 | 0% |
| Acetone + dsRNA IAP-B | 2:1 | 2/26 | 8% |
| Acetone + dsRNA IAP-B | 4:1 | 3/24 | 13% |
| Acetone + dsRNA IAP-B | 8:1 | 3/28 | 11% |
| Acetone + dsRNA IAP-B | 16:1 | 2/55 | 4% |
| 12 hours post application | | | |
| Acetone | 1:0 | 1/30 | 3% |
| Acetone + dsRNA IAP-B | 1:1 | 0/28 | 0% |
| Acetone + dsRNA IAP-B | 2:1 | 3/26 | 12% |
| Acetone + dsRNA IAP-B | 4:1 | 4/24 | 17% |
| Acetone + dsRNA IAP-B | 8:1 | 4/28 | 14% |
| Acetone + dsRNA IAP-B | 16:1 | 3/55 | 5% |
| 24 hours post application | | | |
| Acetone | 1:0 | 1/30 | 3% |
| Acetone + dsRNA IAP-B | 1:1 | 0/28 | 0% |
| Acetone + dsRNA IAP-B | 2:1 | 4/26 | 15% |
| Acetone + dsRNA IAP-B | 4:1 | 4/24 | 17% |
| Acetone + dsRNA IAP-B | 8:1 | 4/28 | 14% |
| Acetone + dsRNA IAP-B | 16:1 | 4/55 | 7% |
| 36 hours post application | | | |
| Acetone | 1:0 | 2/30 | 7% |
| Acetone + dsRNA IAP-B | 1:1 | 0/28 | 0% |
| Acetone + dsRNA IAP-B | 2:1 | 4/26 | 15% |
| Acetone + dsRNA IAP-B | 4:1 | 4/24 | 17% |
| Acetone + dsRNA IAP-B | 8:1 | 4/28 | 14% |
| Acetone + dsRNA IAP-B | 16:1 | 4/55 | 7% |

TABLE 6

Insecticidal activities of dsRNA-IAP-C product against female adults of *Aedes aegypti* by topical application using acetone as a carrier

| Solution | Vol. Ratio of Acetone to dsRNA | Died/Total | Percent Mortality |
|---|---|---|---|
| 4 hours post application | | | |
| Acetone + dsRNA IAP-C | 1:1 | 1/30 | 3% |
| Acetone + dsRNA IAP-C | 2:1 | 2/30 | 7% |
| Acetone + dsRNA IAP-C | 4:1 | 2/30 | 7% |
| Acetone + dsRNA IAP-C | 8:1 | 2/29 | 7% |
| Acetone + dsRNA IAP-C | 16:1 | 3/30 | 10% |
| 12 hours post application | | | |
| Acetone + dsRNA IAP-C | 1:1 | 6/30 | 20% |
| Acetone + dsRNA IAP-C | 2:1 | 3/30 | 10% |
| Acetone + dsRNA IAP-C | 4:1 | 3/30 | 10% |
| Acetone + dsRNA IAP-C | 8:1 | 3/29 | 10% |
| Acetone + dsRNA IAP-C | 16:1 | 4/30 | 13% |
| 24 hours post application | | | |
| Acetone + dsRNA IAP-C | 1:1 | 6/30 | 20% |
| Acetone + dsRNA IAP-C | 2:1 | 5/30 | 17% |
| Acetone + dsRNA IAP-C | 4:1 | 5/30 | 17% |
| Acetone + dsRNA IAP-C | 8:1 | 3/29 | 10% |
| Acetone + dsRNA IAP-C | 16:1 | 6/30 | 20% |
| 36 hours post application | | | |
| Acetone + dsRNA IAP-C | 1:1 | 7/30 | 23% |
| Acetone + dsRNA IAP-C | 2:1 | 6/30 | 20% |
| Acetone + dsRNA IAP-C | 4:1 | 6/30 | 20% |
| Acetone + dsRNA IAP-C | 8:1 | 3/29 | 10% |
| Acetone + dsRNA IAP-C | 16:1 | 6/30 | 20% |

TABLE 7

Insecticidal activities of dsRNA-IAP-D product against female adults of *Aedes aegypti* by topical application using acetone as a carrier

| Solution | Vol. Ratio of Acetone to dsRNA | Died/Total | Percent Mortality |
|---|---|---|---|
| 4 hours post application | | | |
| Acetone + dsRNA IAP-D | 1:1 | 0/30 | 0% |
| Acetone + dsRNA IAP-D | 2:1 | 1/30 | 3% |
| Acetone + dsRNA IAP-D | 4:1 | 0/30 | 0% |
| Acetone + dsRNA IAP-D | 8:1 | 0/30 | 0% |
| Acetone + dsRNA IAP-D | 16:1 | 2/30 | 7% |
| 12 hours post application | | | |
| Acetone + dsRNA IAP-D | 1:1 | 1/30 | 3% |
| Acetone + dsRNA IAP-D | 2:1 | 6/30 | 20% |
| Acetone + dsRNA IAP-D | 4:1 | 3/30 | 10% |
| Acetone + dsRNA IAP-D | 8:1 | 1/30 | 3% |
| Acetone + dsRNA IAP-D | 16:1 | 3/30 | 10% |
| 24 hours post application | | | |
| Acetone + dsRNA IAP-D | 1:1 | 1/30 | 3% |
| Acetone + dsRNA IAP-D | 2:1 | 7/30 | 23% |
| Acetone + dsRNA IAP-D | 4:1 | 3/30 | 10% |
| Acetone + dsRNA IAP-D | 8:1 | 1/30 | 3% |
| Acetone + dsRNA IAP-D | 16:1 | 5/30 | 17% |
| 36 hours post application | | | |
| Acetone + dsRNA IAP-D | 1:1 | 2/30 | 7% |
| Acetone + dsRNA IAP-D | 2:1 | 7/30 | 23% |
| Acetone + dsRNA IAP-D | 4:1 | 3/30 | 10% |
| Acetone + dsRNA IAP-D | 8:1 | 1/30 | 3% |
| Acetone + dsRNA IAP-D | 16:1 | 5/30 | 17% |

TABLE 8

Insecticidal activities of dsRNA-IAP-B + C + D product against female adults of *Aedes aegypti* by topical application using acetone as a carrier

| Solution | Vol. Ratio of Acetone to dsRNA | Died/Total | Percent Mortality |
|---|---|---|---|
| 4 hours post application | | | |
| Acetone + dsRNA IAP-B + C + D | 1:1:1:1 | 6/30 | 20% |
| Acetone + dsRNA IAP-B + C + D | 4:1:1:1 | 5/30 | 17% |
| Acetone + dsRNA IAP-B + C + D | 8:1:1:1 | 2/29 | 7% |
| Acetone + dsRNA IAP-B + C + D | 16:1:1:1 | 2/30 | 7% |
| 12 hours post application | | | |
| Acetone + dsRNA IAP-B + C + D | 1:1:1:1 | 8/30 | 27% |
| Acetone + dsRNA IAP-B + C + D | 4:1:1:1 | 10/30 | 33% |
| Acetone + dsRNA IAP-B + C + D | 8:1:1:1 | 3/29 | 10% |
| Acetone + dsRNA IAP-B + C + D | 16:1:1:1 | 3/30 | 10% |
| 24 hours post application | | | |
| Acetone + dsRNA IAP-B + C + D | 1:1:1:1 | 9/30 | 30% |
| Acetone + dsRNA IAP-B + C + D | 4:1:1:1 | 11/30 | 37% |
| Acetone + dsRNA IAP-B + C + D | 8:1:1:1 | 5/29 | 17% |
| Acetone + dsRNA IAP-B + C + D | 16:1:1:1 | 3/30 | 10% |
| 36 hours post application | | | |
| Acetone + dsRNA IAP-B + C + D | 1:1:1:1 | 9/30 | 30% |
| Acetone + dsRNA IAP-B + C + D | 4:1:1:1 | 11/30 | 37% |
| Acetone + dsRNA IAP-B + C + D | 8:1:1:1 | 6/29 | 21% |
| Acetone + dsRNA IAP-B + C + D | 16:1:1:1 | 3/30 | 10% |

While the invention has been described with reference to details of the illustrated embodiment, these details are not intended to limit the scope of the invention as defined in the appended claims. The embodiment of the invention in which exclusive property or privilege is claimed is defined as follows:

The invention claimed is:

1. A method to control *Aedes aegypti* with double stranded ribonucleic acid, the method comprising: constructing a double stranded ribonucleic acid construct that is complementary to a gene that encodes an inhibitor of apoptosis protein, adding a carrier to the double stranded ribonucleic acid to form a solution, and contacting an effective amount of said solution to *Aedes aegypti* and not an *Aedes aegypti* cell line, wherein RNA interference is induced and *Aedes aegypti* mortality occurs.

2. The method of claim 1, wherein the gene is *Aedes aegypti* inhibitor of apoptosis protein 1 gene.

3. The method of claim 1, wherein the carrier is acetone.

4. The method of claim 1, wherein the carrier is a transfection reagent.

5. The method of claim 1, wherein the solution is applied to *Aedes aegypti* bait material.

6. The method of claim 1, wherein the solution is applied topically to *Aedes aegypti*.

* * * * *

UNITED STATES PATENT AND TRADEMARK OFFICE
CERTIFICATE OF CORRECTION

PATENT NO. : 8,080,648 B1
APPLICATION NO. : 11/716499
DATED : December 20, 2011
INVENTOR(S) : Pridgeon et al.

Page 1 of 1

It is certified that error appears in the above-identified patent and that said Letters Patent is hereby corrected as shown below:

IN THE SPECIFICATION

Column 6, line 43, "are" should be changed to --is--.

Column 6, line 44, "results of three independent experiments" should be changed to --result of one experiment with three duplicates--.

Column 6, line 50, "are" should be changed to --is--.

Column 6, line 51, "results of three independent experiments" should be changed to --result of one experiment with three duplicates--.

Column 6, line 59, "are" should be changed to --is--.

Column 6, line 60, "results of three independent experiments" should be changed to --result of one experiment with three duplicates--.

Signed and Sealed this
Twenty-fourth Day of November, 2015

Michelle K. Lee
*Director of the United States Patent and Trademark Office*

SEQUENCE LISTING

<160> NUMBER OF SEQ ID NOS: 13

<210> SEQ ID NO 1
<211> LENGTH: 40
<212> TYPE: DNA
<213> ORGANISM: Artificial Sequence
<220> FEATURE:
<223> OTHER INFORMATION: T7-IAP1-185F Primer

<400> SEQUENCE: 1

```
taatacgact cactataggg ggctggagtt atgatggctc                            40

<210> SEQ ID NO 2
<211> LENGTH: 36
<212> TYPE: DNA
<213> ORGANISM: Artificial Sequence
<220> FEATURE:
<223> OTHER INFORMATION: T7-IAP1-395R Primer

<400> SEQUENCE: 2
taatacgact cactataggg tggccccacg tagtag                                36

<210> SEQ ID NO 3
<211> LENGTH: 40
<212> TYPE: DNA
<213> ORGANISM: Artificial Sequence
<220> FEATURE:
<223> OTHER INFORMATION: T7-IAP1-375F Primer

<400> SEQUENCE: 3
taatacgact cactataggg gtttctacta cgtggggcca                            40

<210> SEQ ID NO 4
<211> LENGTH: 40
<212> TYPE: DNA
<213> ORGANISM: Artificial Sequence
<220> FEATURE:
<223> OTHER INFORMATION: T7-IAP1-931R Primer

<400> SEQUENCE: 4
taatacgact cactataggg cagcttccca gtctttgagg                            40

<210> SEQ ID NO 5
<211> LENGTH: 40
<212> TYPE: DNA
<213> ORGANISM: Artificial Sequence
<220> FEATURE:
<223> OTHER INFORMATION: T7-IAP-991F Primer

<400> SEQUENCE: 5
taatacgact cactataggg cctcaaagac tgggaagctg                            40

<210> SEQ ID NO 6
<211> LENGTH: 40
<212> TYPE: DNA
<213> ORGANISM: Artificial Sequence
<220> FEATURE:
<223> OTHER INFORMATION: T7-IAP-1347R Primer

<400> SEQUENCE: 6
taatacgact cactataggg gacacaacgg acacttggtg                            40

<210> SEQ ID NO 7
<211> LENGTH: 38
<212> TYPE: DNA
<213> ORGANISM: Artificial Sequence
<220> FEATURE:
<223> OTHER INFORMATION: T7-Cun85-2020F Primer

<400> SEQUENCE: 7
taatacgact cactataggg gaaattcgca agctttac                              38

<210> SEQ ID NO 8
<211> LENGTH: 39
<212> TYPE: DNA
<213> ORGANISM: Artificial Sequence
```

```
<220> FEATURE:
<223> OTHER INFORMATION: T7-Cun85-2640R Primer

<400> SEQUENCE: 8
taatacgact cactataggg tgagcgcaga ttgtggaag                              39

<210> SEQ ID NO 9
<211> LENGTH: 20
<212> TYPE: DNA
<213> ORGANISM: Artificial Sequence
<220> FEATURE:
<223> OTHER INFORMATION: IAP-1133R

<400> SEQUENCE: 9
tgactgaagc gaggatgttg                                                  20

<210> SEQ ID NO 10
<211> LENGTH: 20
<212> TYPE: DNA
<213> ORGANISM: Artificial Sequence
<220> FEATURE:
<223> OTHER INFORMATION: Actin-152F

<400> SEQUENCE: 10
aggactcgta cgtcggtgac                                                  20

<210> SEQ ID NO 11
<211> LENGTH: 18
<212> TYPE: DNA
<213> ORGANISM: Artificial
<220> FEATURE:
<223> OTHER INFORMATION: Actin-590R

<400> SEQUENCE: 11
cgttcagtca ggatcttc                                                    18

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
atggctggag ttatgatggc                                                  20

<210> SEQ ID NO 13
<211> LENGTH: 20
<212> TYPE: DNA
<213> ORGANISM: Artificial
<220> FEATURE:
<223> OTHER INFORMATION: Promoter

<400> SEQUENCE: 13
taatacgact cactataggg                                                  20
```